US00PP15478P2

(12) United States Plant Patent
Cadic

(10) Patent No.: US PP15,478 P2
(45) Date of Patent: Jan. 11, 2005

(54) ***LAVATERA* PLANT NAMED 'INOVERA'**

(50) Latin Name: *Lavatera thuringiacal*
Varietal Denomination: Inovera

(75) Inventor: M. Alain Cadic, Beaucouze (FR)

(73) Assignee: Agri Obtentions S.A., Guyancourt Cedex (FR)

( * ) Notice: Subject to any disclaimer, the term of this patent is extended or adjusted under 35 U.S.C. 154(b) by 0 days.

(21) Appl. No.: 10/634,790

(22) Filed: Aug. 6, 2003

(30) Foreign Application Priority Data

Aug. 7, 2003 (FR) ..... 18218

(51) Int. Cl.[7] ..... A01H 5/00
(52) U.S. Cl. ..... Plt./226
(58) Field of Search ..... Plt./226

(56) References Cited

PUBLICATIONS

UPOV–ROM GTITM Computer Database 2003/06, GTI JOUVE Retrieval Software, citation(s) for 'Inovera'.*

* cited by examiner

*Primary Examiner*—Anne Marie Grunberg
*Assistant Examiner*—Annette H Para
(74) *Attorney, Agent, or Firm*—Burns, Doane, Swecker & Mathis, L.L.P.

(57) ABSTRACT

A new and distinct red-flowered *Lavatera* plant is provided that is a somaclonal mutation of the 'Breedon's Spring' cultivar (non-patented in the United States). Callus culture and regeneration were carried out and the new variety was selected from the resulting plants. The new cultivar can be readily distinguished from the parent cultivar by the presence of larger and deeper pink flowers, a compact well-branched growth habit, and the presence of attractive relatively thick tomentose leaves. The new cultivar also is a tetraploid unlike the parent cultivar.

3 Drawing Sheets

Botanical/commercial classification: *Lavatera thuringiaca/Lavatera* plant.
Varietal denomination: cv. 'Inovera'.

SUMMARY OF THE INVENTION

A new and distinct cultivar of *Lavatera* plant is provided that is somaclonal mutation of the 'Breedon's Spring' cultivar (non-patented in the United States).

When creating the new cultivar of the present invention, plants of the 'Breedon's Spring' cultivar were subjected to callus culture and callus regeneration was conducted. The callus culture and the study of the resulting plants following regeneration were carried out at the Institut National de la Recherche Agronomique located at Angers, France. The initial callus culture was conducted in 1995 and the final selection was made during 1998.

It was found that a single plant observed following such callus culture and regeneration possessed the characteristics of the *Lavatera* plant of the present invention. The characteristics of the new plant can be summarized as follows:

(a) forms attractive larger and deeper pink flowers than the 'Breedon's Spring' cultivar, (b) displays a compact, well-branched growth habit, and (c) forms attractive relatively thick tomentose leaves.

The new cultivar of the present invention well meets the needs of the horticultural industry and is particularly well suited for growing as attractive ornamentation in the landscape.

It has been confirmed through the use of cytometric analysis that the new cultivar is a tetraploid and that the parent 'Breedon's Spring' cultivar is a diploid. The new cultivar also can be readily distinguished from the 'Breedon's Spring' cultivar in view of its denser and compact growth habit, the distinctive larger deeper pink flowers, and the appearance of the leaves. No other tetraploidal

*Lavatera* plants are known by the originator for comparison with the new cultivar.

The new cultivar has been found to readily undergo asexual propagation by the use of cuttings. Roots readily form on such cuttings during the summer. Such asexual propagation has been carried out at Angers, France, and has shown that the cultivar reproduces true to type in subsequent generations.

The new cultivar has been named the 'Inovera' cultivar.

BRIEF DESCRIPTION OF THE PHOTOGRAPHS

The accompanying photographs show three-year old plants of the new cultivar when grown during the summer at Angers, France.

DETAILED DESCRIPTION

The following description is based on the observation of two-year old plants of the new cultivar growing outdoors under typical humidity conditions in very clayey soil at Angers, France. Such plants had been asexually reproduced through the use of cuttings. Reference to The R.H.S. Colour Chart of The Royal Horticultural Society, London, England, is provided. Common color terms are accorded their customary dictionary significance.

Origin: A somaclonal mutation of the 'Breedon's Spring' cultivar (not-patented in the United States).

Plant:

*Habit.*—Compact, erect, and well-branched.

Branches:

*Color.*—At a very early stage the growth is green with traces of anthocyanin coloration. This color quickly darkens with increasing anthocyanin coloration to near Greyed-Purple Group 187A.

*Texture.*—Tomentose.

*Configuration.*—Substantially round in cross section.

*Internode length.*—Approximately 3.75 cm on average.

Foliage:

*General appearance.*—Dark green and vigorous.

*Configuration.*—Primarily trilobal and more or less uniform.

*Margin.*—Commonly wavy and rippled.

*Base.*—Indented.

*Apex.*—Pointed.

*Texture.*—Tomentose and relatively thick.

*Length.*—Approximately 40 to 60 mm on average.

*Width.*—Approximately 40 to 90 mm on average.

*Color.*—Upper surface: Yellow-Green Group 146A. Under surface: Greyed-Green Group 191A.

*Petiole.*—Relatively short, commonly approximately 10 to 15 mm in length on average, and Greyed-Green Group 191B in coloration.

Inflorescence:

*Time of blooming.*—Commonly late spring to early summer blooming is initiated. The first bloom appeared on June 10th in 2003.

*Duration of blooming.*—Approximately five weeks on average.

Figure 1:
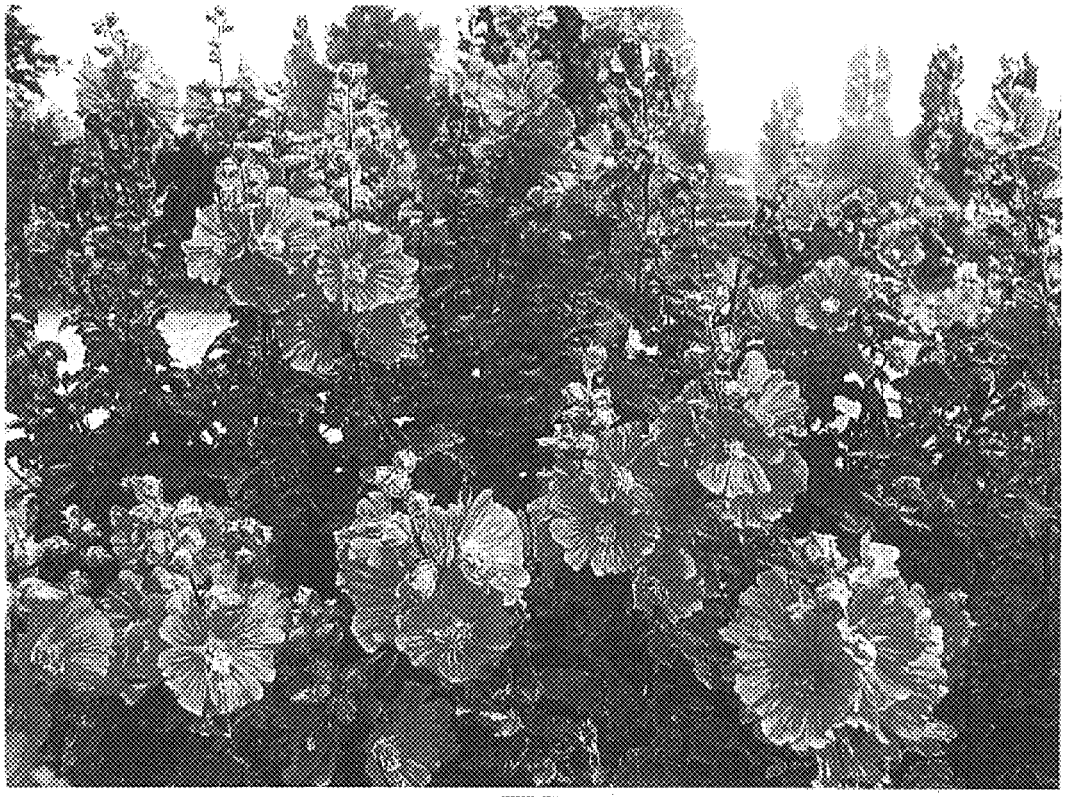
FIG. 1 shows the typical foliage and blossoms in various stages of opening of the new cultivar.
Figure 2:
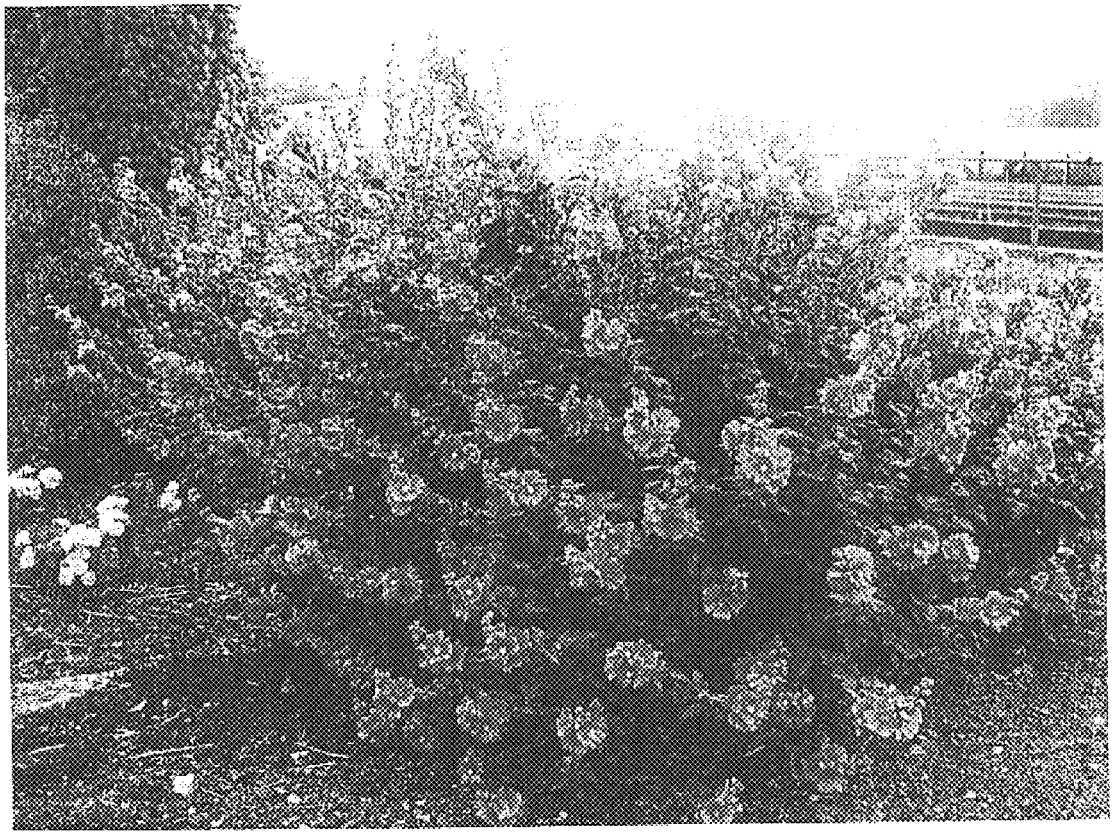
FIG. 2 shows the typical overall branching character and compact growth habit of the new cultivar.
Figure 3:
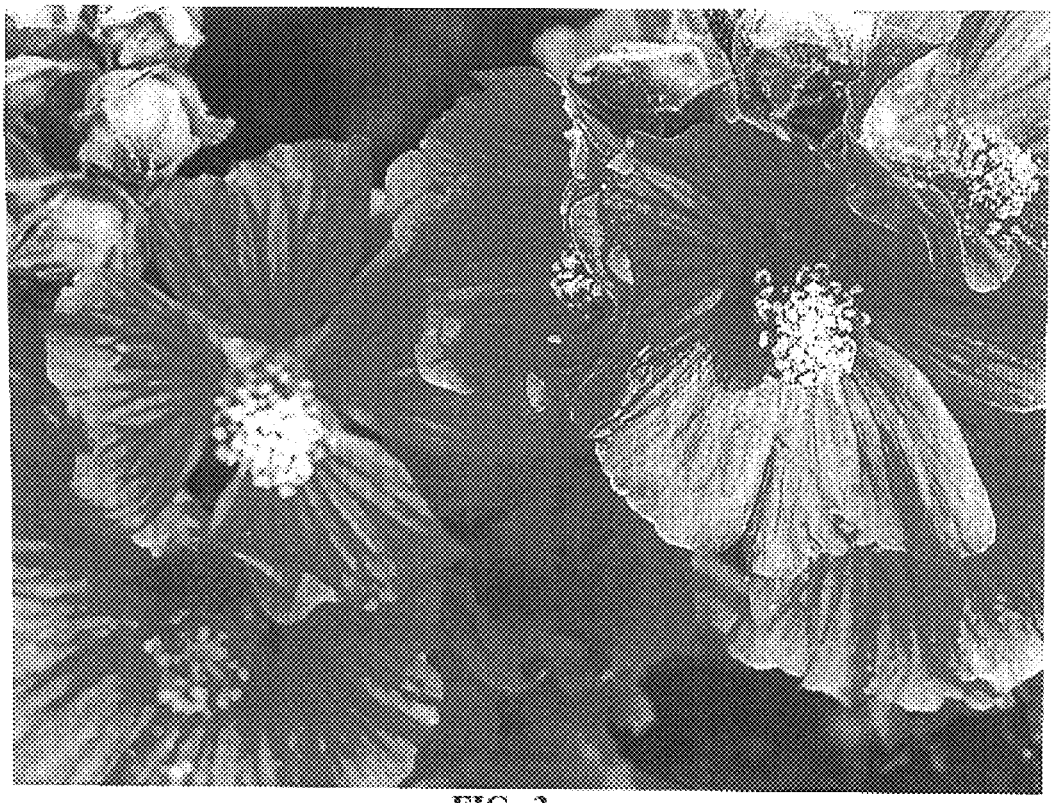
FIG. 3 shows a closer view of the larger attractive pink flowers of the new cultivar.

*Buds.*—Tomentose in appearance (See FIG. 1), when vegetative Greyed-Green Group 191C, and when flowering commonly bears an apex of Red-Purple Group 74A.

*Size.*—A fully open flower commonly measures approximately 6 cm in diameter.

*Configuration.*—Flowers are regular and rounded.

*Petal number.*—Five.

*Petal consistency.*—Firm but flexible.

*Petal shape.*—Rounded with the petal edges being joined at the base.

*Color.*—Upper surface: near Red-Purple Group 73A and veined with near Red-Purple Group 72C. Under surface: predominantly near Red-Purple Group 70B and the veins are near Red-Purple Group 70B and less apparent.

*Lastingness of a flower.*—Commonly approximately 5 to 8 days on average depending upon the environmental conditions.

*Stamens.*—Approximately 50 or more on average.

*Filaments.*—Approximately 4 mm in length where separate and free and fused at the base in the shape of a tube having a length of approximately 9 to 11 mm, and near Red-Purple Group 72B in coloration.

*Anthers.*—Generally kidney-shaped in configuration, approximately 0.5 mm in size on average, and generally purple in coloration when young changing to grayish with maturity.

*Pollen.*—Plentiful and whitish in coloration.

*Pistils.*—Approximately 20 on average.

*Stigma.*—Approximately 7 mm in size on average, and near Red-Purple Group 62C in coloration.

*Styles.*—Approximately 22 mm in length, and near Red-Purple Group 62C in coloration.

*Sepals.*—Smooth, tomentose, approximately 15 mm in length, joined at the base with five spade-shaped tips having lengths of approximately 7 mm, and almond green in coloration.

*Hips.*—The sepals are joined at the base and develop the fruit. The fruit commonly consists of 25 to 50 seeds arranged in a circle around the axis of the bloom. Dense silk-like hairs are present and the general appearance is almond green with traces of anthocyanin. The color commonly is Greyed-Yellow Group 160D at the base and near Greyed-Green Group 194B towards the tip.

No particular susceptibility to plant diseases or to insects has been noted during observations to date.

Plants of the new 'Inovera' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Lavatera* plant that is a somaclonal mutation of the 'Breedon's Spring' cultivar having the following combination of characteristics:

(a) forms attractive larger and deeper pink flowers than the 'Breedon's Spring' cultivar, (b) displays a compact, well-branched growth habit, and (c) forms attractive relatively thick tomentose leaves, substantially as illustrated and described.

* * * * *